United States Patent [19]

Ratcliffe

[11] 4,211,707
[45] Jul. 8, 1980

[54] PROCESS FOR HYDROLYTICALLY CLEAVING O-SULFO THIENAMYCINS

[75] Inventor: Ronald W. Ratcliffe, Matawan, N.J.

[73] Assignee: Merck & Co., Inc., Rahway, N.J.

[21] Appl. No.: 932,739

[22] Filed: Aug. 10, 1978

[51] Int. Cl.² ............................................ C07D 487/04
[52] U.S. Cl. .............................. 260/326.31; 546/256; 546/272; 424/274
[58] Field of Search .................................... 260/326.31

[56] References Cited
PUBLICATIONS

Maeda et al., Jour. of Antibiotics, vol. XXX, No. 9, (9/1977), pp. 770–772.

Primary Examiner—Mary C. Lee
Attorney, Agent, or Firm—Hesna J. Pfeiffer; James A. Arno; Julian S. Levitt

[57] ABSTRACT

Disclosed is a process for the hydrolytically cleaving O-sulfo thienamycins:

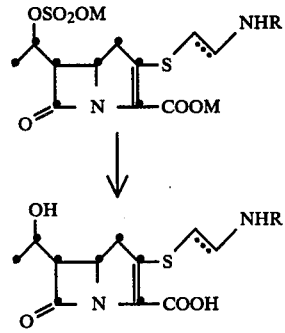

wherein R is H or acetyl and M is H, an alkali or alkaline earth metal cation or an organo cationic species such as pyridinium; and wherein the dotted line indicates saturated and unsaturated species.

1 Claim, No Drawings

PROCESS FOR HYDROLYTICALLY CLEAVING O-SULFO THIENAMYCINS

BACKGROUND OF THE INVENTION

This invention relates to the hydrolytic cleavage of O-sulfate esters of a group of antibiotics known as the thienamycins:

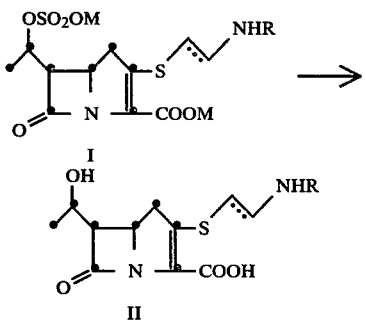

both species I and II are antibiotics, wherein R is H or acetyl and M is H, an alkali or alkaline earth metal action or an organo cationic species such as pyridinium, and wherein the dotted line indicates saturated and unsaturated species. Starting materials I are known and available to the art. The final products are also known and available to the art. In addition to published references, starting materials I are disclosed and claimed in co-pending, commonly assigned U.S. Patent Applications Ser. Nos. 006,959 (filed 1-5-79) which is a continuation of Ser. No. 860,662 (filed 12-15-77) now abandoned; 860,665 (filed 12-15-77); 891,799 (filed 3-30-78) and 893,846 (filed 4-6-78); which are incorporated herein by reference.

DETAILED DESCRIPTION OF THE INVENTION

The above indicated scheme of reaction is preferably conducted in a polar solvent such as dioxane, dimethylsulfoxide, pyridine, dimethylformamide, or the like in the presence of a trace of water (from 0.1 to about 1% water). Typically the reaction is conducted at a temperature of from 25° to 100° C. for from 5 mins to 20 hrs. The following examples illustrate the process of the present invention and the recovery of the desired carbinol.

EXAMPLE 1

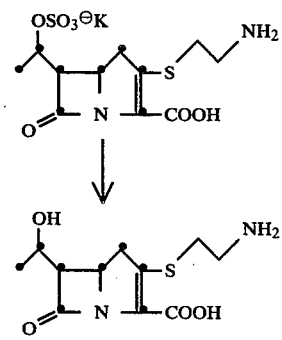

A suspension of potassium O-sulfo-6-(1-hydroxyethyl)-2-(2-aminoethylthio)-1-carbadethiapen-2-em-3-carboxylic acid (50 mg) in dioxane (2.5 ml) is stirred and heated at 50° C. for 4 hrs. The mixture is diluted with water (5 ml), concentrated under vacuum to ca. 1 ml, and charged onto a Dowex 50-X4 column (sodium form). Elution with deionized water gives fractions containing 6-(1-hydroxyethyl)-2-(2-aminoethylthio)-1-carbadethiapen-2-em-3-carboxylic acid which are pooled, concentrated under vacuum and lyophilized. Following the procedure of Example 1 except substituting an equivalent amount of the N-acetyl derivative for the starting material, there is obtained the corresponding N-acetyl, free carbinol product:

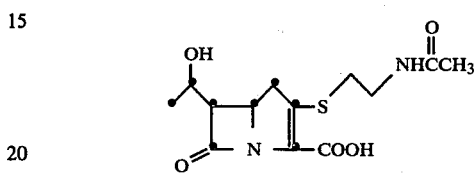

EXAMPLE 2

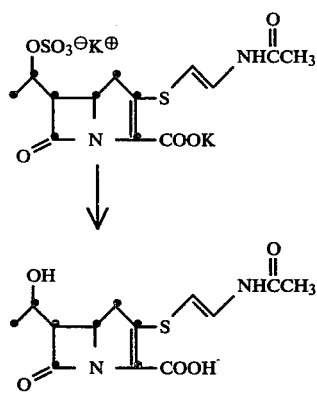

A suspension of dipotassium N-acetyl-O-sulfo-6-(1-hydroxyethyl) -2-(2-aminovinylthio)-1-carbadethiapen-2-em-3-carboxylate (50 mg) in dioxane (2 ml) is stirred at room temperature for 20 hrs. The mixture is diluted with water (5 ml), concentrated under reduced pressure to ca. 1 ml, and charged onto a XAD-2 column. The column is eluted with water and 5% THF in water. The appropriate fractions are pooled, concentrated under vacuum, and lyophilized to yield potassium N-acetyl-6-(1-hydroxyethyl)-2-(2-aminovinylthio) -1-carbadethiapen-2-em-3-carboxylate.

What is claimed is:

1. A process for preparing a compound having the structure:

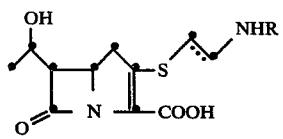

and its pharmaceutically acceptable salts and esters which comprises hydrolyzing a compound having the formula:

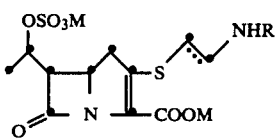

wherein M is H⊕, an alkali or alkaline earth metal cation or an organic cation; R is hydrogen or acetyl and the dotted line indicates provision for both saturated and unsaturated species;

the hydrolyzing is conducted in a solvent selected from the group consisting of: dioxane, dimethylformamide, dimethylsulfoxide, or pyridine in the presence of 0.1 to 1% water at a temperature of from 25° to 100° C.

* * * * *